United States Patent [19]
Ueda

[11] Patent Number: 5,454,826
[45] Date of Patent: Oct. 3, 1995

[54] TEMPORARY CLIP WITH BALLOON ACTIVATION MEANS FOR CONTROLLING BLOOD FLOW

[75] Inventor: Shinsuke Ueda, Yokohama, Japan

[73] Assignee: Mineluba Co., Ltd., Tokyo, Japan

[21] Appl. No.: 202,439

[22] Filed: Feb. 25, 1994

[30] Foreign Application Priority Data

Feb. 26, 1993 [JP] Japan ................................ 5-061258
Nov. 22, 1993 [JP] Japan ................................ 5-313967

[51] Int. Cl.⁶ .............................................. A61B 17/122
[52] U.S. Cl. ........................................ 606/158; 606/151
[58] Field of Search ........................ 128/DIG. 19, 20, 128/23; 604/96; 606/1, 139, 142, 151, 157, 158, 191, 194, 202, 203, 204–211; 227/902

[56] References Cited

U.S. PATENT DOCUMENTS

| | | | |
|---|---|---|---|
| 3,538,917 | 11/1970 | Selker | 606/158 |
| 3,579,751 | 5/1971 | Jonckheere | 606/158 |
| 3,802,437 | 4/1974 | Kees | 606/151 |
| 4,586,501 | 5/1986 | Claracq | 606/158 |
| 4,708,140 | 11/1987 | Baron | 606/201 |
| 4,800,879 | 1/1989 | Golyakhovsky et al. | 606/158 |
| 5,234,459 | 8/1993 | Lee | 606/203 |
| 5,236,437 | 8/1993 | Wilk et al. | 606/158 |
| 5,250,074 | 10/1993 | Wilk et al. | 606/158 |

FOREIGN PATENT DOCUMENTS

| | | | |
|---|---|---|---|
| 0319261 | 7/1918 | Germany | 606/203 |

*Primary Examiner*—Stephen C. Pellegrino
*Assistant Examiner*—Glenn Dawson
*Attorney, Agent, or Firm*—Price, Heneveld, Cooper, DeWitt & Litton

[57] ABSTRACT

A temporary clip for controlling blood flow comprises a balloon for exerting clipping or clip-releasing force when inflated. A tube is connected to the balloon to inject into or sucks fluid from the balloon to inflate or deflate the balloon. The fluid pressure in the balloon is remote-controlled.

9 Claims, 5 Drawing Sheets

TEMPORARY CLIP WITH BALLOON ACTIVATION MEANS FOR CONTROLLING BLOOD FLOW

BACKGROUND OF THE INVENTION

The present invention relates to a temporary clip for controlling blood flow in an object artery.

In neurosurgery, clips are used for controlling bleeding of arteries. Some clips are left permanently or semi-permanently at their site of clipping, and others are removed as soon as their purpose are over. Clips removed after use are called temporary clips.

For example, when a premature rupture of cerebral aneurysm occurs before a clear vision of a site of operation is obtained, blood stanching by temporary clipping is necessary. In such temporary clipping, clipping pressure differs for different object arteries. And, in a bleeding of a large quantity during operation, quick clipping is necessary, but it is a rather difficult and troublesome work to confirm a bleeding site and apply temporary clipping to the confirmed site after a bleeding of a large quantity. Therefore, it is desired that a loosened clip is placed beforehand at an anticipated temporary clip site and that the clip is quickly tightened by remote control when bleeding begins.

Besides, since peripheral circulation is not to be disturbed for a long time, a temporary clip must be repeatedly tightened and loosened at a same site.

Heretofore, a same clip has been used for permanent and temporary clipping, and various types of temporary clips are to be prepared for various clipping pressure. And heretofore used temporary clips are not adapted either to be placed beforehand or to be repeatedly tightened and loosened by remote control.

SUMMARY OF THE INVENTION

Therefore, an object of this invention is to provide a remote-controlled temporary clip wherein clipping pressure can be changed by remote control.

Another object of this invention is to provide a temporary clip adapted to be placed beforehand at an anticipated clipping site in a loosened state and to be tightened promptly when clipping is required.

Still another object of this invention is to provide a temporary clip adapted to be repeatedly tightened and loosened at a same clipping site.

Still another object of this invention is to provide a remote-controlled temporary clip wherein clipping pressure is indicated on a pressure gauge.

And still another object of this invention is to provide an automatic-controlled temporary clip wherein clipping pressure is automatically controlled to a value preset in a pressure controller.

In order to achieve these objects, an inflatable balloon is used to control clipping pressure of temporary clipping. An inflator/deflator injects fluid into or sucks from the balloon through a flexible tube.

These and other objects, features and advantages of the present invention will become clear from the following description of the preferred embodiments in conjunction with the accompanying drawings in which the same numerals indicate the same or the corresponding parts.

DETAILED DESCRIPTION OF THE PREFERRED EMBODIMENTS

Figure 7:
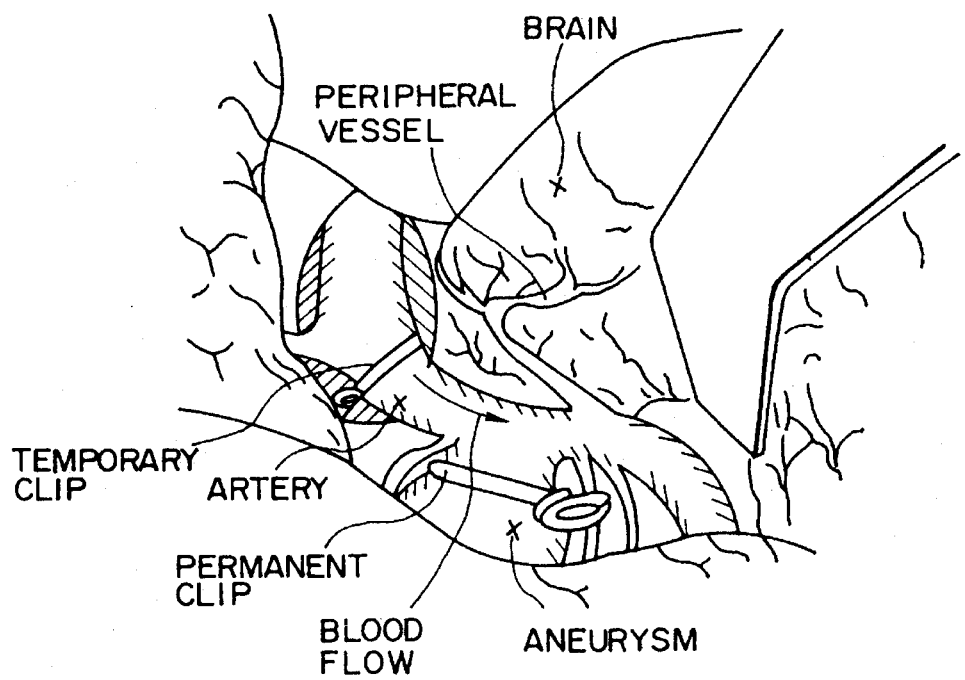
FIG. 7 shows an example of temporary clipping.

Referring to FIG. 7, there is shown an example of temporary clipping used in neurosurgery. An aneurysm is detected by diagnoses. Neck of the aneurysm is to be clipped by a permanent clip to stop further bleeding. When there is a premature rupture, the artery supplying bleeding blood is clipped by a temporary clip, and as soon as the necessity of the temporary clipping is over, the temporary clipping is released to allow blood flow in peripheral vessels.

Referring to FIG. 1, an embodiment of a temporary clip of this invention comprises a clip body 1, a balloon 3, a flexible tube 4, and a pressure controller 50.

The clip body 1 comprises a first member 11, a second member 12, a pin 18 for supporting these first and second members at a common supporting point, and a spring 2. The first member 11 and the second member 12 have shapes roughly symmetrical to each other, each composed of a curved portion and a handle portion.

The pin 13 serves as an axis of rotation of the first and the second members 11,12. The spring 2 exerts elastic force in a direction for closing both ends 111, 121 of the curved portions of the first and the second members 11, 12, forming a circular space between the two curved portions.

Figure 1A:
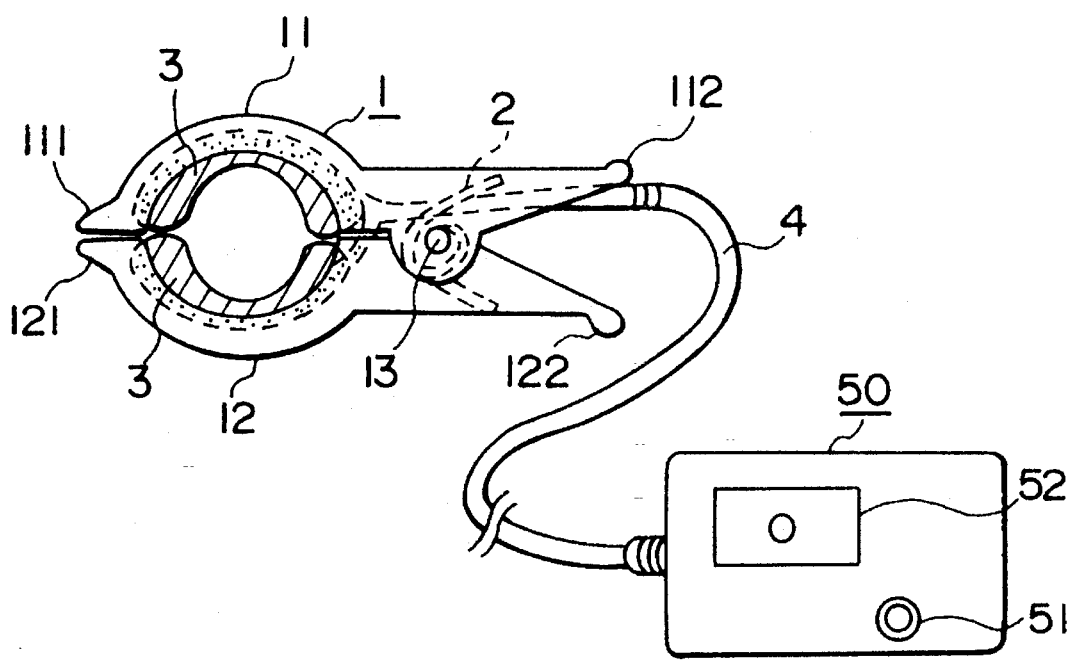
FIGS. 1A and 1B show an arrangement of a temporary clip of an embodiment of this invention wherein clipping pressure is automatically controlled.

The curved portions have grooves in their inner surfaces for containing the balloon 3. When the balloon 3 is deflated, only a small portion of the balloon 3 comes out from the grooves leaving an ample space between the two curved portions as shown in FIG. 1A.

With a manual force applied at both ends 112, 122 of the handle portions, the ends 111, 121 of the curved portions are opened, and the clip body 1 can be easily placed at an anticipated site of temporary clipping. With the balloon 3 deflated as shown in FIG. 1A, the circular space between the curved portions is wide enough for holding an object artery loosely in the space.

Figure 1B:
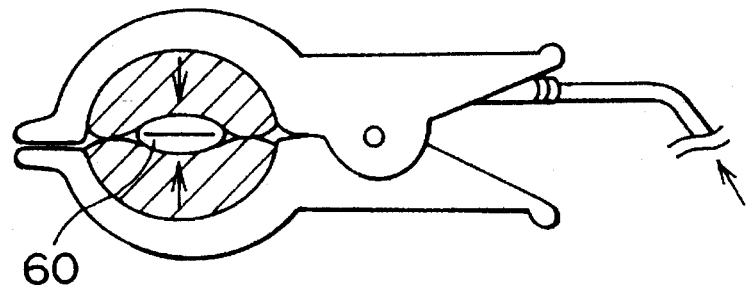

When the balloon 3 is inflated, the balloon 8 expands into the circular space since the expansion into an outward direction is obstructed by the curved portions. And, as shown by FIG. 1B, the inflated balloon 3 clips the object artery 60.

Clipping pressure of this temporary clip is automatic-controlled by the pressure controller 50. This clipping pressure is varied by varying pressure setting 51, and is indicated by a pressure gauge 52 provided in the pressure controller 50.

For removing clipping of this temporary clip, the balloon 3 is deflated to come to a state shown in FIG. 1A. This remote control of removing clipping eliminates manual operations which may be in the way of a field of sight of operation.

Either pneumatic pressure or hydraulic pressure will be used for inflating the balloon 3, and as for the pressure controller 50, any conventional pneumatic or hydraulic pressure controller can be used.

Figure 2A:
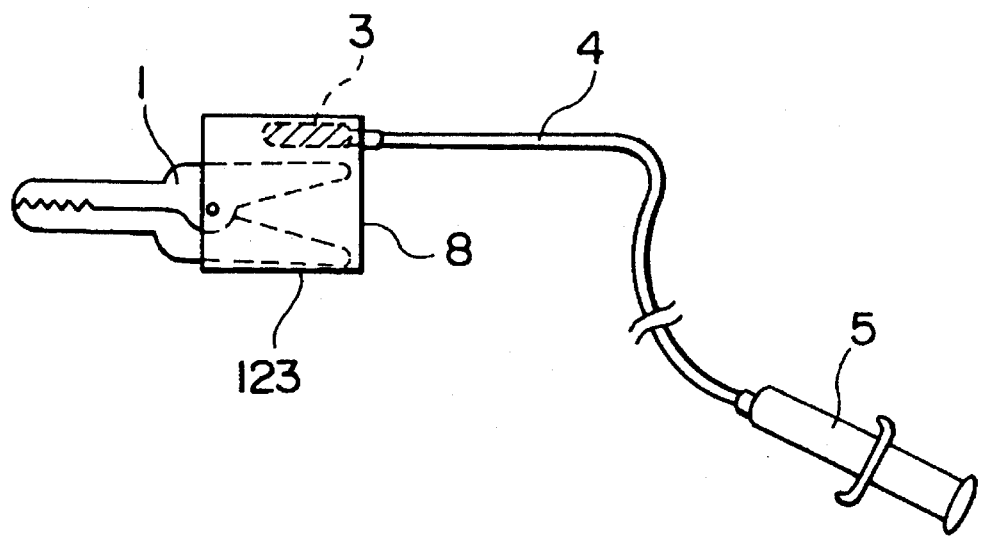
FIGS. 2A and 2B show an arrangement of a temporary clip of another embodiment of this invention.

In an embodiment shown in FIGS. 2, each of the first member and the second member of the clip body 1 has a grasping jaw portion and a handle portion. A spring (not shown) exerts elastic force in a direction of pressing the two grasping jaw portions against each other.

A balloon container 8 contains a balloon 3. A side 123 of a handle of the clip body 1 is fixed to a side of the balloon container 8. Balloon container 8 acts as a link mechanism between balloon 3 and the clip body 1.

Figure 2B:
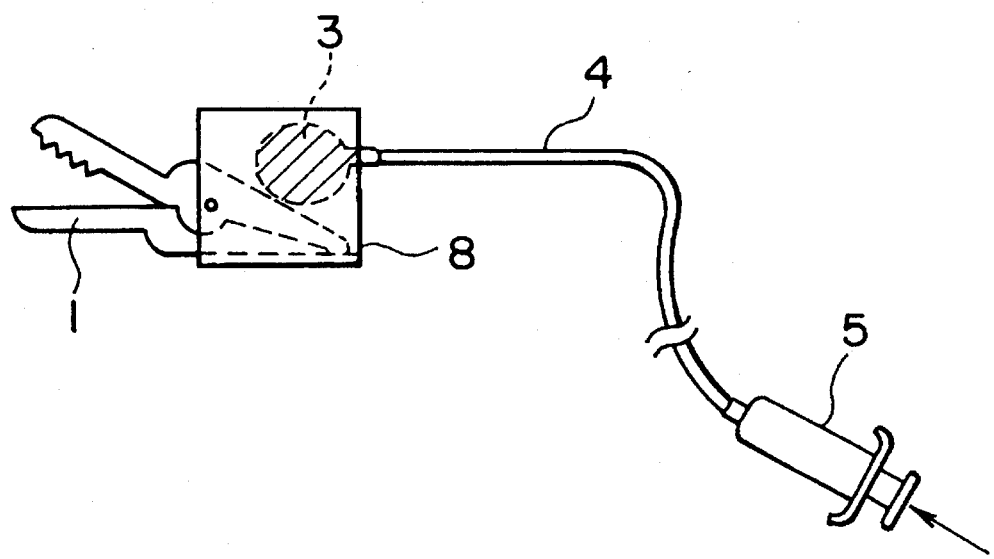

In placing this clip of FIGS. 2 at an anticipated clipping site, the balloon 3 is inflated by pressing fluid from a manually actuated syringe 5 connected at another end of the flexible tube 4. The syringe 5 works as an inflator/deflator of the balloon 3. The jaw portions are opened as shown in FIG. 2B. In the opened jaw portion, an object artery is loosely held. When the balloon 3 is deflated, the jaw portion is closed by the elastic force of spring, and the clipping pressure can be controlled by controlling the pressure in the balloon 3 which exerts a force opposing to that of the spring.

Figure 3:
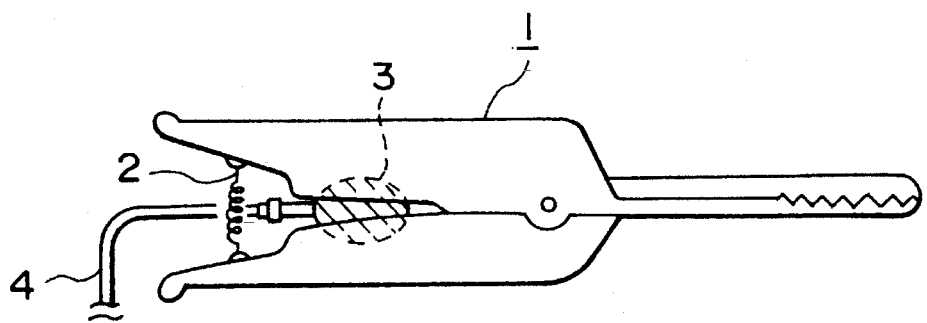
FIGS. 3A and 3B show an arrangement of a temporary clip of still another embodiment of this invention.
Figure 3:
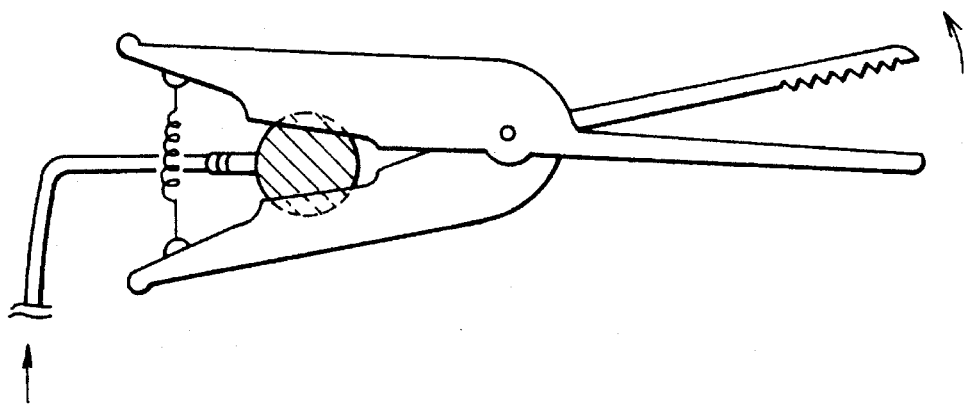

In an embodiment shown in FIGS. 3, the clip body 1 is similar to that shown in FIGS. 2, but the handles of the first and the second members have grooves for containing the balloon 3. When the balloon 3 is inflated, the grasping jaw portion is opened as shown by FIG. 3B. The temporary clip shown by FIGS. 3 works in a same way with that shown by FIGS. 2

In these embodiments shown in FIGS. 2 and FIGS. 3, the pressure controller 50 of FIG. 1A may be connected at another end of the flexible tube 4. But, these types of clip body 1 as shown in FIGS. 2 and FIGS. 3 are usually used for on-off control of clipping, and clipping pressure is determined by an elastic force of the spring 2. And for such on-off control of clipping, a manual control by a syringe is convenient.

Figure 4:
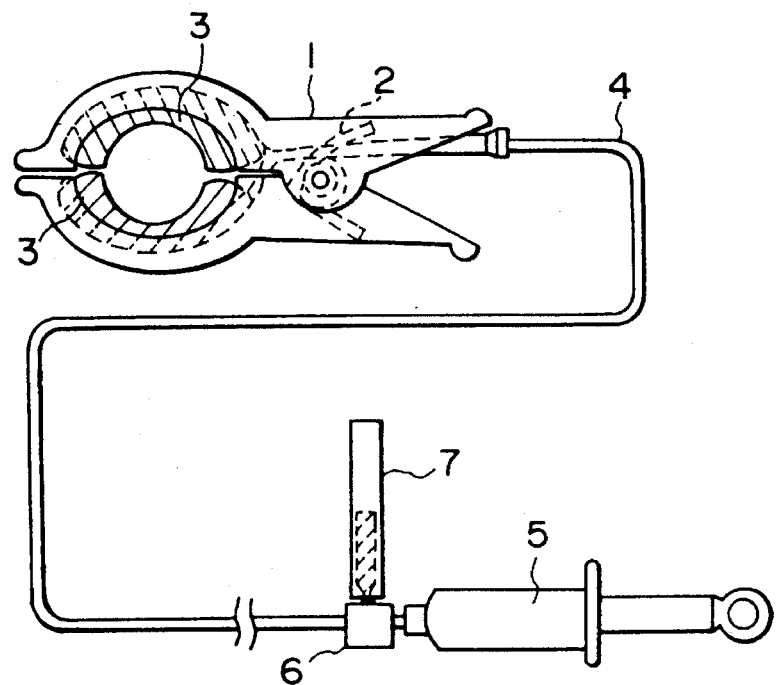
FIG. 4 shows a modification of FIG. 1, wherein a pressure controller is changed to a manually operated inflator/deflator.

FIG. 4 shows a modification of an embodiment shown in FIGS. 1. In an embodiment shown in FIG. 4, a manually controlled syringe 5 is used as an inflator/deflator of the balloon 3, and a pressure gauge 7 is connected to the flexible tube 4 by a gauge connector 6. In this embodiment, clipping pressure is manually controlled and is indicated by the pressure gauge 7.

Figure 5:
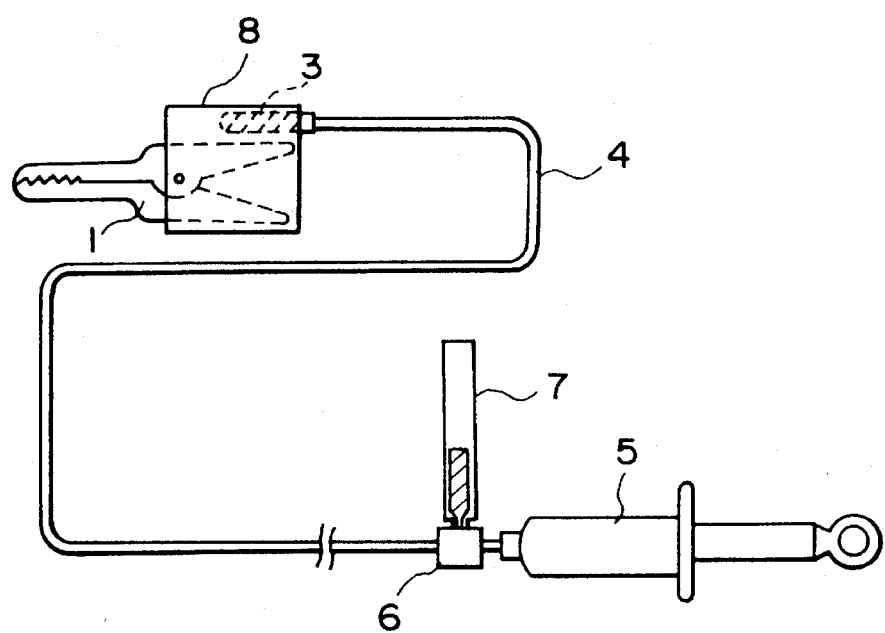
FIG. 5 shows a modification of FIG. 2, wherein a pressure gauge is provided.

FIG. 5 shows a modification of an embodiment shown in FIGS. 2. In an embodiment shown in FIG. 5, a pressure gauge 7 is connected to the flexible tube 4 by a gauge connector 6. In this embodiment, pressure in the balloon 3 is indicated by the pressure gauge 7. The clipping pressure is a difference pressure between the elastic force of a spring and the pressure in the balloon 3, and the pressure gauge 7 may be graduated by this difference.

Figure 6:
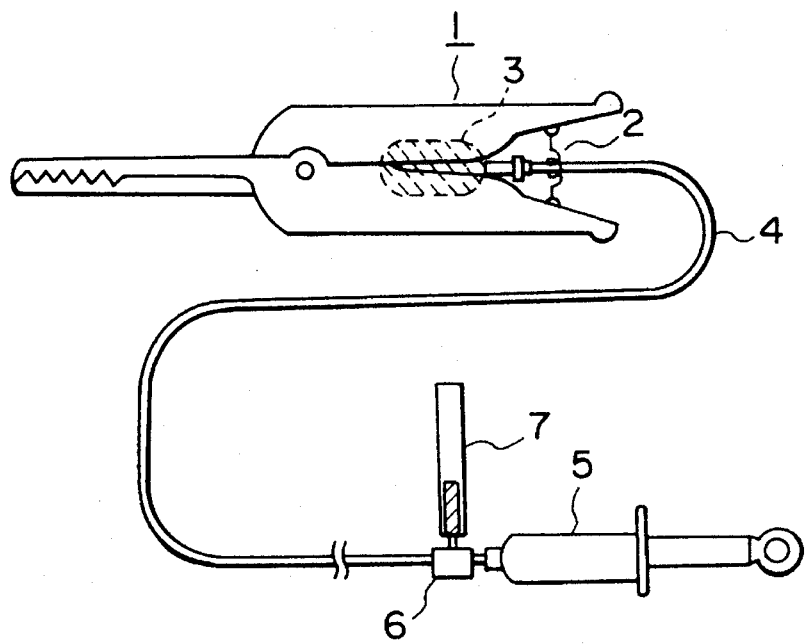
FIG. 6 shows a modification of FIG. 3, wherein a pressure gauge is provided.

And FIG. 6 shows a modification of an embodiment shown in FIGS. 3. In this embodiment, the pressure in the balloon 3 is indicated by a pressure gauge 7.

Although only preferred embodiments are described in this specification, it should be understood that various changes and modifications may be made without departing from the spirit of this invention.

What is claimed is:

1. A temporary clip for controlling blood flow in an artery comprising:

a balloon for exerting force when inflated;

a flexible tube coupled to said balloon for conveying pressurized fluid to said balloon;

an inflator/deflator coupled to said tube for injecting said pressurized fluid into said tube or withdrawing said pressurized fluid from said tube, in order to inflate or deflate said balloon;

a clip body for grasping the artery by applying a grasping force to the artery, said clip body comprising a first member and a second member, each of said members having a grasping jaw portion and a handle, a pin for supporting said members at a common supporting point in their handles and serving as an axis of rotation of said members, and a spring for exerting elastic force to said members in a direction for pressing the two grasping jaw portions together to grasp an object artery between the grasping jaw portions, and a link mechanism coupled to said clip body and operably coupled to said balloon for converting an adjustment of said force of said balloon to an adjustment of said clip body grasping force, said link mechanism comprising a balloon container in which a side of one of said member handles is fixed, and in which said balloon is contained for exerting force when inflated to the other of said member handles which is not fixed to said balloon container in a direction for opening said two grasping jaw portions, whereby the grasping force of the clip is adjusted using said inflator/deflator.

2. A temporary clip for controlling blood flow in an artery, comprising:

a clip body configured to grasp an artery, said clip body comprising a first body member and a second body member, each of said body members having an artery grasping portion and a handle, said first body member and said second body member pivotably coupled so as to pivot said artery grasping portions relative to one another between an open position and a closed position, and a spring mounted on said clip body to bias said artery grasping portions of said first body member and said second body member toward one of said open position and said closed position;

a balloon operably coupled to said clip body proximate at least one of said handles of said body members, said balloon disposed and configured so as to be urged against said at least one of said handles and exert force thereon as said balloon is inflated and thereby urge said artery grasping portions toward the other of said open position and said closed position as said balloon is inflated;

a tube operably coupled to said balloon so as to convey fluid to said balloon;

a fluid source including a fluid supply operably coupled to said tube and adapted to inject fluid into said tube and withdraw fluid from said tube, thereby inflating and deflating said balloon;

whereby said artery grasping portions are shifted between said open position and closed position by said spring and said balloon, and pressure is applied to an artery by said temporary clip and adjusted by adjusting the amount of fluid in said balloon by said fluid source.

3. A temporary clip of claim 2, wherein said fluid source comprises a pressure controller for automatically controlling pressure in said tube at a value preset on a pressure setting provided in said pressure controller.

4. A temporary clip of claim 3, wherein said pressure controller comprises a pressure gauge for indicating pressure in said tube.

5. A temporary clip of claim 2, wherein said fluid source comprises a syringe operably coupled to said tube for injecting said fluid into said tube or withdrawing said fluid from said tube.

6. A temporary clip of claim 5, wherein said fluid source further comprises a pressure gauge operably coupled with said tube for indicating pressure in said tube.

7. A temporary clip for controlling blood flow in an artery according to claim 2, further comprising a container, and wherein said handles of said body members and said balloon are mounted in said container, a first of said handles is fixed relative to said container, and said balloon is disposed to be urged against a second of said handles when said balloon is inflated.

8. A temporary clip for controlling blood flow in an artery according to claim 2, wherein each of said handles of said body members includes an inner side surface and a groove on said inner side surface thereof configured to contain a portion of said balloon therein, and said handles are urged apart as said balloon is inflated.

9. A temporary clip for controlling blood flow in an artery according to claim 2, wherein said body members are coupled by a single pin pivotably coupling said body members at a common supporting point serving as an axis of rotation of said body members.

* * * * *